US011097067B2

(12) United States Patent
Yeh (10) Patent No.: US 11,097,067 B2
(45) Date of Patent: Aug. 24, 2021

(54) INJECTION PEN

(71) Applicant: CC Biotechnology Corporation, Tainan (TW)

(72) Inventor: Chin-Min Yeh, Tainan (TW)

(73) Assignee: CC Biotechnology Corporation, Tainan (TW)

( * ) Notice: Subject to any disclaimer, the term of this patent is extended or adjusted under 35 U.S.C. 154(b) by 129 days.

(21) Appl. No.: 16/607,425

(22) PCT Filed: Apr. 25, 2017

(86) PCT No.: PCT/CN2017/081827
§ 371 (c)(1),
(2) Date: Oct. 23, 2019

(87) PCT Pub. No.: WO2018/195764
PCT Pub. Date: Nov. 1, 2018

(65) Prior Publication Data
US 2020/0129705 A1    Apr. 30, 2020

(51) Int. Cl.
*A61M 5/32* (2006.01)
*A61M 5/315* (2006.01)
(52) U.S. Cl.
CPC ........ *A61M 5/321* (2013.01); *A61M 5/31535* (2013.01); *A61M 5/31571* (2013.01); *A61M 5/31576* (2013.01); *A61M 5/3202* (2013.01)
(58) Field of Classification Search
CPC .............. A61M 5/321; A61M 5/31535; A61M 5/31571; A61M 5/3202; A61M 5/3204;
(Continued)

(56) References Cited

U.S. PATENT DOCUMENTS 7,118,553 B2    10/2006 Scherer
7,635,350 B2    12/2009 Scherer
(Continued)

FOREIGN PATENT DOCUMENTS

WO    WO2008005315 A2    1/2006

*Primary Examiner* — Nathan R Price
*Assistant Examiner* — Tasnim Mehjabin Ahmed
(74) *Attorney, Agent, or Firm* — Alan D. Kamrath; Karin L. Williams; Mayer & Williams PC (57) ABSTRACT

An injection pen comprises a starting mechanism (1) and a driving mechanism (2). A needle pin (40) of the starting mechanism (1) fitted to a connecting rod (30) and a front spring (60) is disposed in a front housing (10) and an inner casing (20) therein. A front cover (50) is disposed at the front end of the front housing (10) and covers the needle pin (40). A rear housing (70) of the driving mechanism (2) and a driving casing (80) therein are connected to the front housing (10). A trigger tube (90) and a key panel (A0) are mounted in the driving casing (80). A push rod (A1) fitted to a rear spring (A2) is mounted in the trigger tube (90). An elastic baffle (83) of the driving casing (80) fastens the driving casing (80) and the push Rod (A1) and locks the rear spring (A2). An injection needle group (3) can be mounted between the starting mechanism (1) and the driving mechanism (2). When the front cover (50) is removed, the needle pin (40) can be pressed and inwards retreated into the front housing (10) to make a needle (3A) to be exposed, and the inwards retreated needle pin (40) drives the connecting rod (30) to push away the elastic baffle (83) of the driving casing (80) to perform unlocking. The released rear spring (A2) pushes the push rod (A1) to make an injection needle group (3) to transfer a drug. After the injection, the needle pin (40) is reset under the push of the front spring (60), and the needle pin (40) is fastened in the inner casing (20) when a key panel (A0) is pulled out by means of the connecting rod (30), so that the needle pin (40) cannot be pressed to inwards
(Continued)

retreat, and accordingly, a used syringe needle (3A) is protected, so as to prevent users from being hurt by the needle by accident.

20 Claims, 11 Drawing Sheets (58) Field of Classification Search
CPC ............... A61M 5/3157; A61M 5/326; A61M 5/31576; A61M 2005/3267; A61M 2005/2013; A61M 2005/2407; A61M 2005/2414

See application file for complete search history.

(56) References Cited

U.S. PATENT DOCUMENTS

| | | | |
|---|---|---|---|
| 7,927,303 B2* | 4/2011 | Wyrick | A61M 5/2033 604/117 |
| 8,343,110 B2* | 1/2013 | Harrison | A61M 5/2033 604/218 |
| 8,529,510 B2 | 9/2013 | Giambattista et al. | |
| 9,132,242 B2 | 9/2015 | Kemp et al. | |
| 9,486,584 B2 | 11/2016 | Julian et al. | |
| 9,623,181 B2 | 4/2017 | Brereton et al. | |
| 9,770,558 B2 | 9/2017 | Bumell et al. | |
| 9,814,839 B2 | 11/2017 | Eaton | |
| 9,981,086 B2 | 5/2018 | Cowe et al. | |
| 10,105,496 B2 | 10/2018 | Aneas | |
| 2013/0324925 A1 | 12/2013 | Brereton et al. | |
| 2016/0015896 A1* | 1/2016 | Cowe | A61M 5/31571 604/198 |
| 2016/0331905 A1* | 11/2016 | Aneas | A61M 5/3234 |
| 2018/0078709 A1* | 3/2018 | Yeh | A61M 5/3202 |

* cited by examiner

INJECTION PEN

BACKGROUND OF THE INVENTION

1. Field of the Invention

The present invention relates to an injection pen, especially to an injection pen that can prevent a user from an accidental needle stick and has a dose control effect.

2. Description of Related Art

A conventional injection pen is applied to be combined with a syringe having medication contained therein and a needle. After removal of a needle cap or a plug, the needle can be inserted into the skin of a human body and the medication is injected into the human body via the needle by pushing a pushing rod mounted on a rear end of the injection pen to drive a piston inside the syringe to move with a transmission of a driving mechanism. After injection, the needle cap or the plug is attached around the needle again, and the syringe is discarded.

However, the conventional injection pen is a tool for subcutaneous injection, but the conventional injection pen has problems of safety and laboriousness. When the injection is done, the needle cap or the plug has to be attached around the needle manually by a user, and the user is easily stuck by the needle. In addition, while injecting medication, the pushing rod has to be pushed manually to move the piston in the syringe to move with a transmission of the driving mechanism and to inject medication into the human body, so the operation of the conventional injection pen is laborious.

To overcome the shortcomings of the conventional dose metering syringe, the present invention provides an injection pen to mitigate or obviate the aforementioned problems.

SUMMARY OF THE INVENTION

The main objective of the present invention is to provide an injection pen to solve the aforementioned problems of safety and laboriousness.

To achieve the above objective, the injection pen has an actuating mechanism and a driving mechanism connected with the actuating mechanism, wherein the actuating mechanism comprises a front casing having an assembling space defined axially through the front casing;

an inner casing mounted in the assembling space in the front casing and having a front segment, a rear segment, and a baffle disposed between the front segment and the rear segment and having an inner hole, two first through holes, and two second through holes, wherein the two first through holes and the two second through holes are located around the inner hole;

a connection rod mounted moveably in the inner casing and comprising a rod body having an axial hole defined axially through the rod body;

two hooks formed on a rear end of the rod body at positions corresponding respectively to the first through holes of the inner casing; and two actuating portions formed on the rear end of the rod body and extending respectively through the second through holes of the inner casing;

a needle hub mounted moveably in the front casing, connected with the connection rod, and having a tubular body and an outer sleeve formed around a front end of the tubular body, being located in front of a front end of the front casing, and being retractable into the front casing;

a front cap mounted detachably around the outer sleeve of the needle hub and abutting the front end of the front casing; and a front spring mounted in the front segment of the inner casing, held between the actuating portions of the connection rod, and having two ends abutting the connection rod and the inner casing, respectively; and the driving mechanism comprises a rear casing being hollow and mounted on a rear end of the front casing;

a driving casing mounted securely in the rear casing, extending into the front casing, and having a receiving space formed axially through the driving casing and two resilient engaging tabs;

a driving tube mounted in the driving casing and having
  a tube hole formed in a rear end of the driving tube;
  an end board formed on a front end of the driving tube and having a through bore defined through the end board and communicating with the tube hole; and
  two side holes defined radially in an outer surface of the driving tube, communicating with the tube hole, and selectively engaged with the resilient engaging tabs of the driving casing, wherein the actuating portions of the connection rod selectively extend into the driving tube to disengage the resilient engaging tabs from the side holes;

two engaging members mounted in the driving casing and mounted around a front end of the driving tube, and each engaging member having
  two engaging hooks formed on a front end of the engaging member, selectively extending through the first through holes in the inner casing, respectively, and selectively engaged with the hooks on the connection rod; and
  two resilient locking portions formed on a rear end of the engaging member and engaged with the driving casing, wherein the engaging members are selectively pushed by the connection rod to move and to engage with the first through holes in the inner casing;

a pushing rod mounted in the driving tube and having a first rod segment mounted through the through bore in the end board of the driving tube, a second rod segment, and a middle board formed between the first rod segment and the second rod segment and abutting the two resilient engaging tabs that are engaged with the side holes in the driving tube; and a rear spring mounted in the driving tube, mounted around the second rod segment of the pushing rod, and having two ends abutting the middle board and the rear casing, respectively.

Wherein, the driving casing further has two engaging recesses defined in an inner surface of the driving casing and being diametrically opposite each other; and two guiding recesses defined in the inner surface of the driving casing and being diametrically opposite each other;

the engaging recesses and the guiding recesses in the driving casing are arranged in an alternate manner;

the resilient engaging tabs of the driving casing correspond respectively to the guiding recesses in position;

the actuating portions of the connection rod are mounted respectively through the guiding recesses and selectively push the actuating portions, respectively, to swing outward; and the resilient locking portions of each engaging member are engaged detachably with the engaging recesses in the driving casing.

Wherein, the two first through holes and the two second through holes in the inner casing are arranged in an alternate manner;

the first through holes are diametrically opposite each other;

the second through holes are diametrically opposite each other;

the baffle of the inner casing has an inner tube formed on a front side of the baffle and extending into the front segment of the inner casing;

the inner hole in the baffle extends into the inner tube; and the front spring is mounted around the inner tube.

Wherein, the two first through holes and the two second through holes in the inner casing are arranged in an alternate manner;

the first through holes are diametrically opposite each other;

the second through holes are diametrically opposite each other;

the baffle of the inner casing has an inner tube formed on a front side of the baffle and extending into the front segment of the inner casing;

the inner hole in the baffle extends into the inner tube; and the front spring is mounted around the inner tube.

Wherein, the front casing has a window formed radially in an outer surface of a front segment of the front casing and communicating with the assembling space;

the front segment of the inner casing comprises two wings diametrically opposite each other and spaced at a spaced interval;

the interval between the wings is equal to a width of the window in the front casing; and the connection rod has an elongated hole defined in the rod body of the connection rod and corresponding to the window in the front casing in position.

Wherein, the front casing further has two engaging holes defined in a rear segment of the front casing;

the rear casing has two extension tabs formed on a front end of the rear casing and extending into the rear segment of the front casing;

each extension tab has an engaging protrusion selectively engaged with a respective one of the engaging holes in the front casing and a fixing hole defined in the extension tab; and the driving casing has two fixing blocks formed on an outer surface of the driving casing and engaged respectively with the fixing hole in the rear casing to securely mount the driving casing in the rear casing.

Wherein, the front casing further has two engaging holes defined in a rear segment of the front casing;

the rear casing has two extension tabs formed on a front end of the rear casing and extending into the rear segment of the front casing;

each extension tab has an engaging protrusion selectively engaged with a respective one of the engaging holes in the front casing and a fixing hole defined in the extension tab;

the driving casing has two fixing blocks formed on an outer surface of the driving casing and engaged respectively with the fixing hole in the rear casing to securely mount the driving casing in the rear casing;

the rod body of the connection rod further has two resilient tabs formed on an outer surface of the rod body and being diametrically opposite each other; and the tubular body of the needle hub further has two tab holes defined in the tubular body and engaged respectively with the resilient tabs on the rod body of the connection rod to connect the connection rod with the needle hub.

Wherein, the front cap comprises a cap body mounted around the outer sleeve of the needle hub and having a closed front end and an open rear end abutting the front end of the front casing; and a connection tube formed in the cap body, extending out of the open rear end of the cap body, extending into the tubular body of the needle hub, and having a rear end provided with a hook and at least one slit defined in the rear end of the connection tube.

The present invention can achieve the following advantages:

1. A syringe can be conveniently assembled with the injection pen that comprises pre-assembled actuating mechanism and the driving mechanism.

2. In the injection pen, the needle hub connected with the connection rod and the front spring of the actuating mechanism is mounted in the front casing and the inner casing, and the front cap is mounted on the front end of the front casing and is mounted around the needle hub. The driving tube and the engaging members are mounted in the driving casing, and the pushing rod connected with the rear spring is mounted in the driving tube. The engaging tabs of the driving casing are applied to engage the driving casing with the connection rod to lock the rear spring. With such an arrangement, after the syringe is mounted between the actuating mechanism and the driving mechanism and the front cap is removed, the needle hub can be pressed to enable the needle to be exposed and the needle can be pierced into the skin of a human body. The connection rod can be moved to push and to disengage the resilient tabs on the driving casing by the retracted needle hub. The released rear spring can push the pushing rod to push the piston to move forward. Accordingly, the syringe can inject the medication in a predetermined dose.

3. After the injection pen is used, the needle hub can be pushed to the original position by the front spring and to enclose the needle. The engaging members can be moved to engage with the inner casing by the connection rod, such that the needle hub can be prevented from retracting into the front casing again. Accordingly, needle stick injuries by the used needle can be prevented.

In addition, the injection pen in accordance with the present invention can also keep the unused needle from being retracted by the front cap mounted on the front end of the front casing and around the needle hub. The safety of using the injection pen can be improved.

The injection pen in accordance with the present invention can move the connection rod rearward by the pressed needle hub until the hooks on the connection rod extend into the first through holes and are engaged with the engaging hooks on the engaging members to generate sounds. After the engaging members are moved by the connection rod, the locking portions on the engaging members will be engaged with the baffle on the inner casing to generate sounds by the movement of the connection rod.

DETAILED DESCRIPTION OF PREFERRED EMBODIMENT

Figure 1:
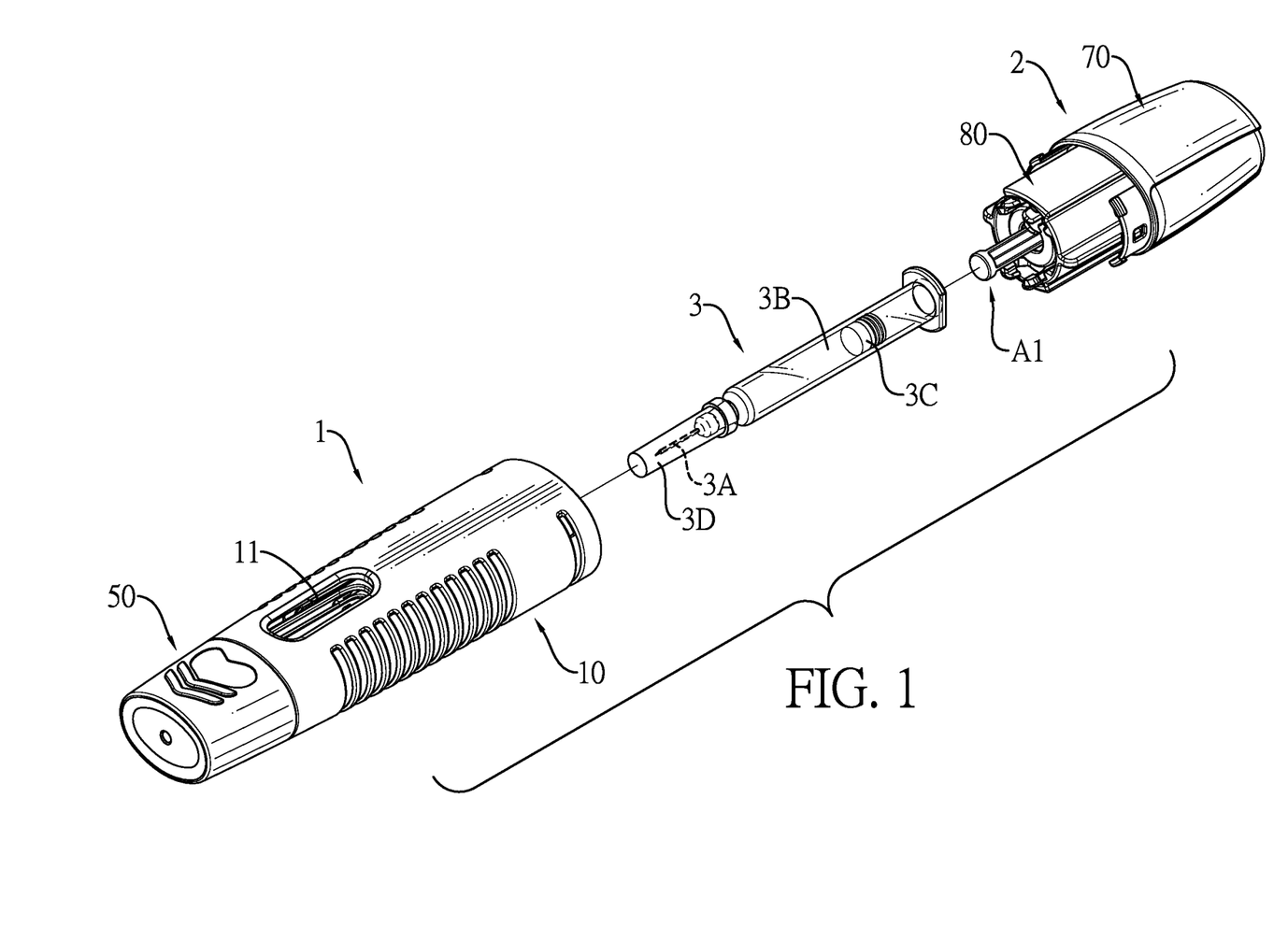
FIG. 1 is an exploded perspective view of an injection pen in accordance with the present invention with a syringe.
Figure 2:
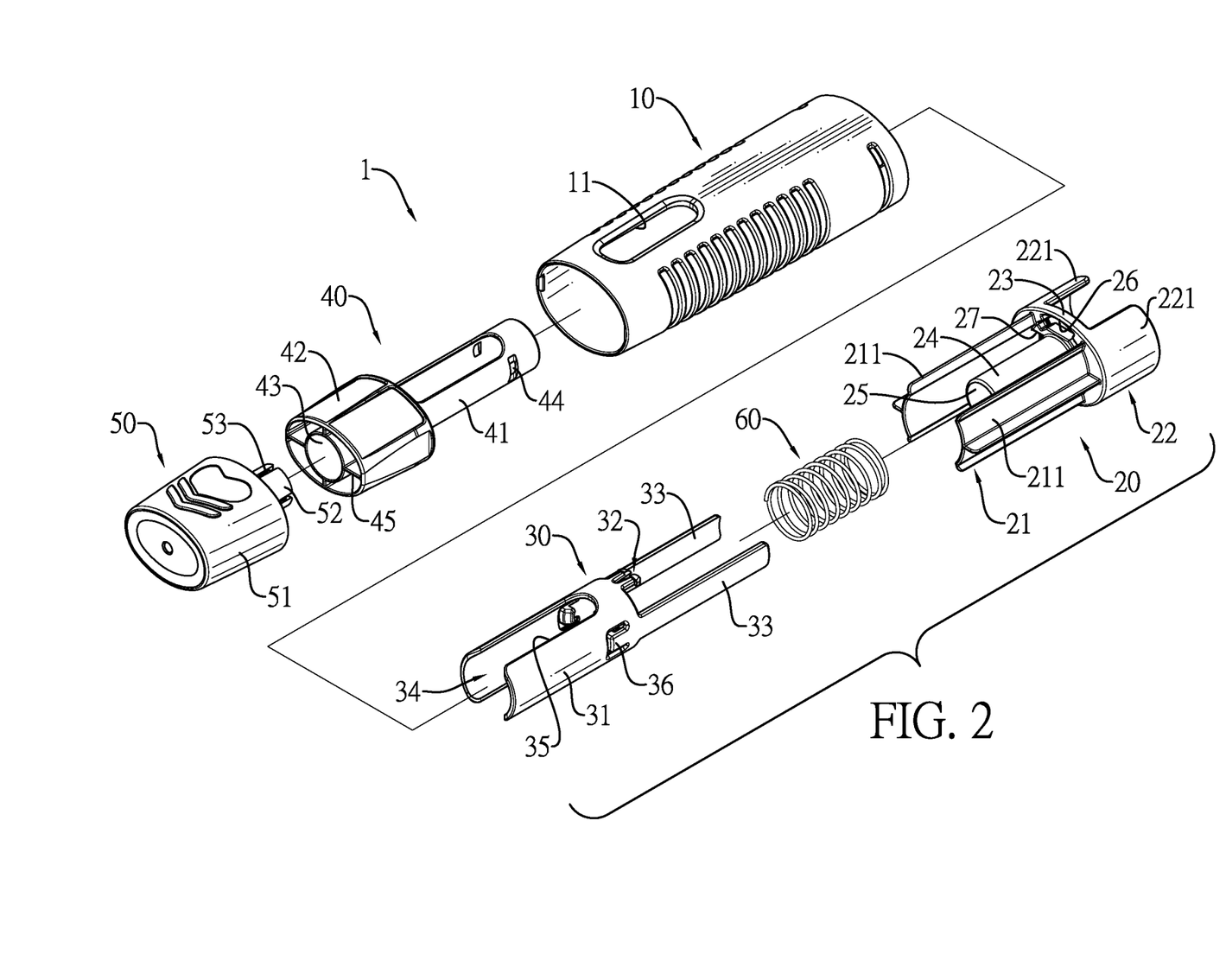
FIG. 2 is an exploded perspective view of the actuating mechanism of the injection pen in FIG. 1.
Figure 3:
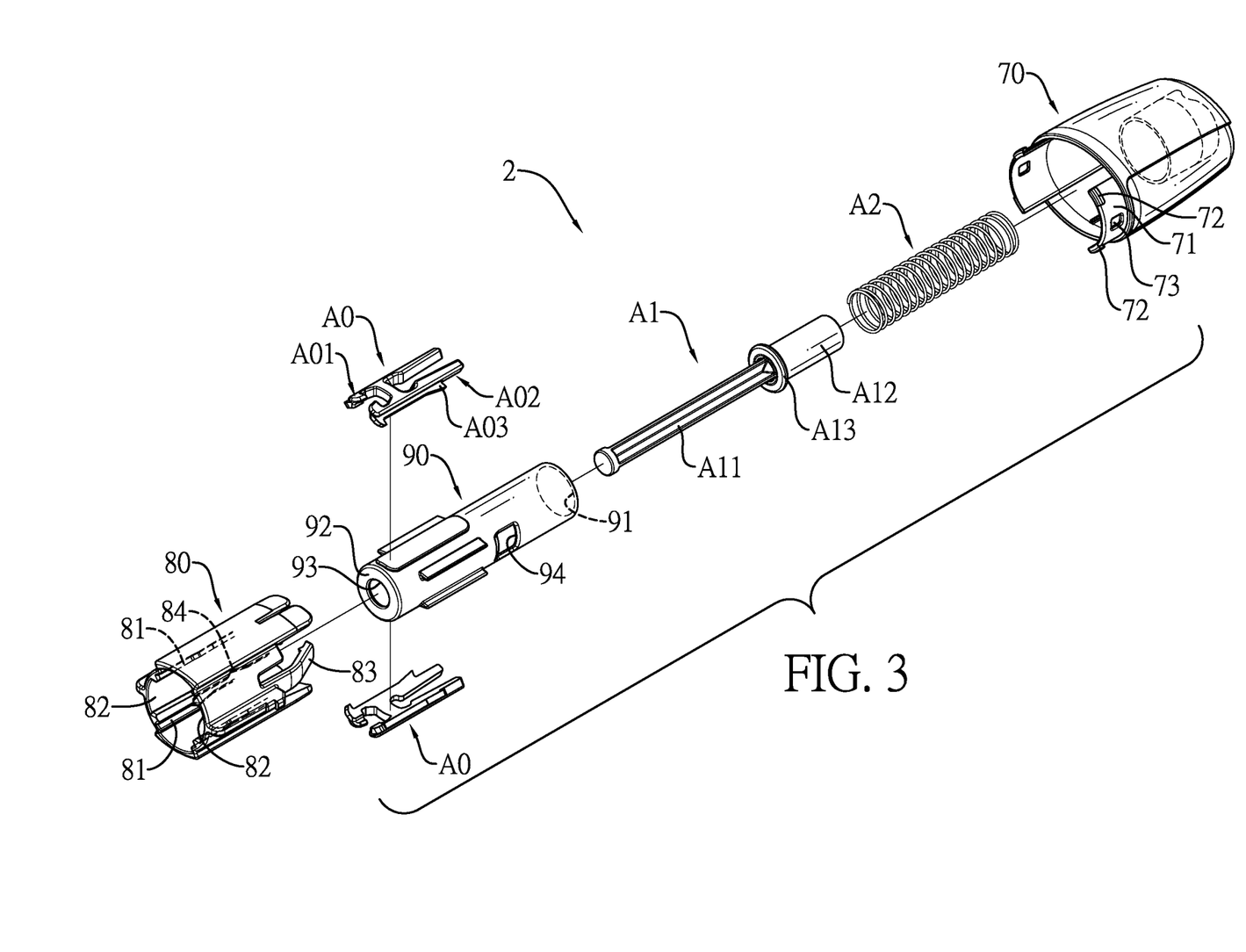
FIG. 3 is an exploded perspective view of the driving mechanism of the injection pen in FIG. 1.

With the reference to FIG. 1, a preferred embodiment of an injection pen in accordance with the preset invention is shown for combining with a syringe 3 to inject medication and comprises an actuating mechanism 1 and a driving mechanism 2.

With reference to FIGS. 1, 2, 4, and 5, the actuating mechanism 1 comprises a front casing 10, an inner casing 20, a connection rod 30, a needle hub 40, a front cap 50, and a front spring 60.

With reference to FIGS. 1, 2, 4, and 5, the front casing 10 has an assembling space defined axially through the front casing 10. In the embodiment, a window 11 is formed radially in an outer surface of a front segment of the front casing 10 and communicates with the assembling space. Two engaging holes 12 are defined in a rear segment of the front casing 10.

With reference to FIGS. 1, 2, 4, and 5, the inner casing 20 is mounted in the front casing 10. The front end of the inner casing 20 is spaced from the front end of the front casing 10 at a spaced interval. The inner casing 20 comprises a front segment 21, a rear segment 22, and a baffle 23. The front segment 21 and the rear segment 22 are formed respectively on the front end and the rear end of the inner casing 20. The baffle 23 is disposed between the front segment 21 and the second segment 22. The baffle 23 further has an inner tube 24 formed on a front side of the baffle 23 and extending into the front segment 21. An inner hole 25 is defined in the baffle 23 and the inner tube 24. The baffle 23 further has two first through holes 26 and two second through holes 27 located around the inner tube 24. The two first through holes 26 and the two second through holes 27 are arranged in an alternate manner. The two first through holes 26 are diametrically opposite each other, and the two second through holes 27 are diametrically opposite each other.

With reference to FIGS. 1, 2, 4, and 5, in the embodiment, the front segment 21 of the inner casing 20 comprises two front wings 211 diametrically opposite each other and spaced at a spaced interval. The interval between the front wings 211 is equal to a width of the window 11 in the front casing 10. The rear segment 22 comprises two rear wings 221 diametrically opposite each other and spaced at a spaced interval. The front wings 211 are respectively aligned with the rear wings 221.

With reference to FIGS. 1, 2, 4, and 5, the connection rod 30 is mounted in the inner casing 20 and is mounted around the inner tube 24. The connection rod 30 comprises a rod body 31, two hooks 32, and two actuating portions 33. An axial hole 34 is defined axially through the rod body 31. The hooks 32 and the actuating portions 33 are formed on a periphery of a rear end of the rod body 31 and are arranged in an alternate manner. The hooks 32 correspond respectively to the first through holes 26 in the inner casing 20 in position. The actuating portions 33 extend respectively through the second through holes 27 in the inner casing 20. An elongated hole 35 is formed in the rod body 31, or two elongated holes 35 are defined in the rod body 31 and are diametrically opposite each other as shown in the embodiment. The elongated hole 35 corresponds to the window 11 of the front casing 10 in position. Two resilient tabs 36 are formed on an outer surface of the rod body 31 and are diametrically opposite each other.

With reference to FIGS. 1, 2, 4, and 5, the needle hub 40 is mounted in the front casing 10, is connected with the connection rod 30 to move with the connection rod 30, and moveably extends out of the front end of the front casing 10. The needle hub 40 has a tubular body 41 and an outer sleeve 42. The outer sleeve 42 has dimensions larger than those of the tubular body 41, is formed around a front end of the tubular body 41, and is located in front of the connection rod 30. A central hole 43 is defined axially through the tubular body 41. The tubular body 41 is inserted securely into the rod body 31 of the connection rod 30 to move with the connection rod 30. In the embodiment, the tubular body 41 further has two tab holes 44 defined in the tubular body 41 and engaged respectively with the resilient tabs 36 on the rod body 31. Multiple reinforcing ribs 46 are formed between the inner surface of the outer sleeve 42 and the outer surface of the tubular body 41.

Figure 4:
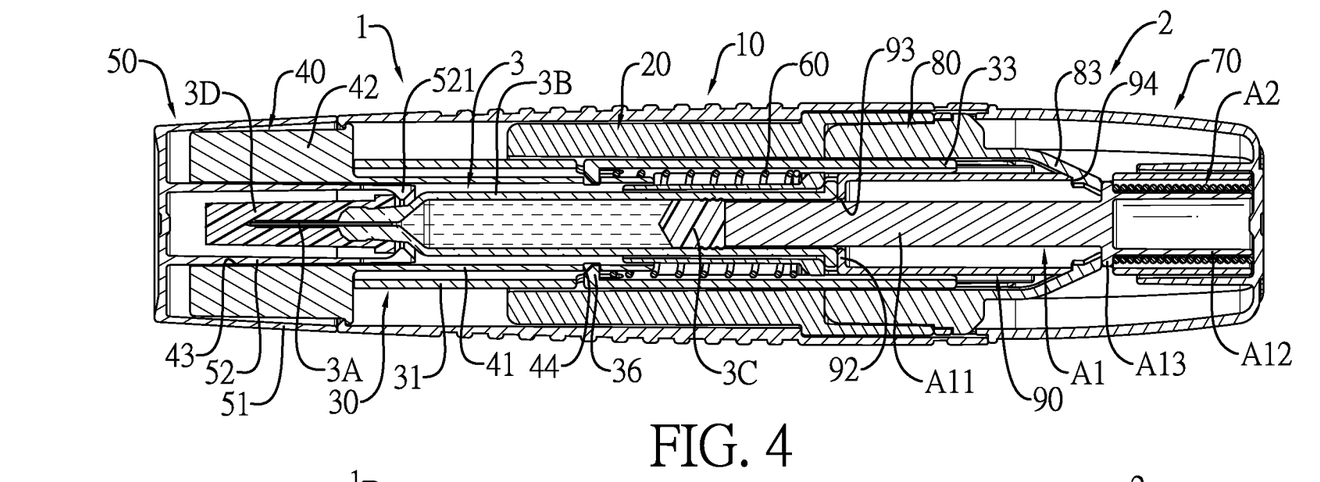
FIG. 4 is a cross sectional top view of the injection pen in FIGS. 1 to 3 combined with the syringe.
Figure 5:
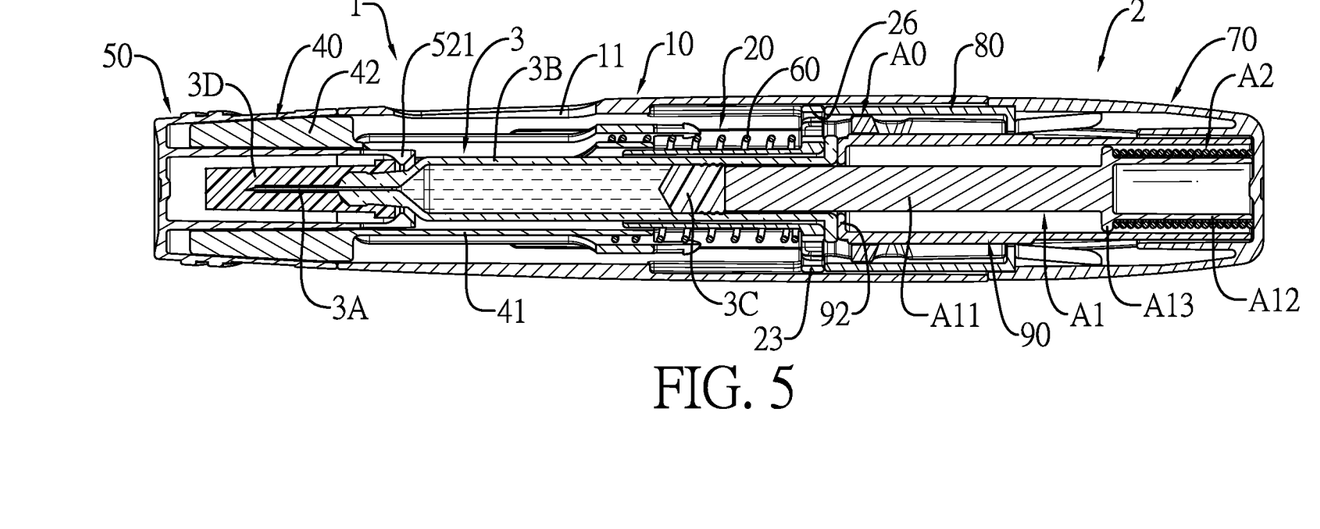
FIG. 5 is a cross sectional side view of the injection pen in FIGS. 1 to 3 combined with the syringe.

With reference to FIGS. 1, 2, 4, and 5, the front cap 50 is mounted detachably around the needle hub 40 and abuts the front end of the front casing 10. The front cap 50 comprises a cap body 51 and a connection tube 52. The cap body 51 has a closed front end and an open rear end. The cap body 51 is mounted around the outer sleeve 42 of the needle hub, and the open rear end of the cap body 51 abuts the front end of the front casing 10. The connection tube 52 is formed in the cap body 51, extends out of the open rear end of the cap body 51, and extends into the central hole 42 in the tubular body 41 of the needle hub 40. The connection tube 52 has at least one slit 53 defined in the rear end of the connection tube 52 to allow the rear end of the connection tube 52 to have resilience. With reference to FIGS. 4 and 5, in the embodiment, the rear end of the connection tube 52 may be provided with a hook 521.

With reference to FIGS. 1, 2, 4, and 5, the front spring 60 is mounted in the front segment 21 of the inner casing 20 and is mounted around the inner tube 24. The actuating portions 33 are disposed around the front spring 60. The front spring 60 has two ends abutting respectively the connection rod 30 and the inner casing 20 to allow the front spring 60 to be compressed and to provide a resilient force to the connection rod 30.

With reference to FIGS. 1. 3, 4, and 5, the driving mechanism 2 is mounted on a rear end of the actuating mechanism 1 and comprises a rear casing 70, a driving casing 80, a driving tube 90, two engaging members A0, a pushing rod A1, and a rear spring A2.

With reference to FIGS. 1, 3, 4, and 5, the rear casing 70 is assembled on the rear end of the front casing 10 of the actuating mechanism 1 and has a closed rear end and an open front end. The rear casing 70 further has two extension tabs 71 formed on the front end of the rear casing 70 and extending into the rear segment of the front casing 10. Each extension tab 71 has an engaging protrusion 72 selectively engaged with a respective one of the engaging holes 12 in the front casing 10 to securely attach the rear casing 70 onto the rear end of the front casing 10 and a fixing hole 73 defined in the extension tab 71.

With reference to FIGS. 1, 3, 4, and 5, the driving casing 80 is mounted securely in the rear casing 70 and extends into the front casing 10 and the rear segment 22 of the inner casing 20 of the actuating mechanism 1. The driving casing 80 has a receiving space formed axially through the driving casing 10, two engaging recesses 81, two guiding recesses 82, two resilient engaging tabs 83, and two fixing blocks 84. The engaging recesses 81 are defined in an inner surface of the driving casing 80 and are diametrically opposite each other, and the guiding recesses 82 are defined in the inner surface of the driving casing 80 and are diametrically opposite each other. The engaging recesses 81 and the guiding recesses 82 are arranged in an alternate manner. The engaging tabs 83 are diametrically opposite each other and correspond respectively to the guiding recesses 82 in position. The fixing blocks 84 are formed on an outer surface of the driving casing 80 and engaged respectively with the fixing hole 73 in the rear casing 70 to securely mount the driving casing 80 in the rear casing 70. The actuating portions 33 of the connection rod 30 are mounted respectively through the guiding recesses 82 to allow the actuating portions 33 to push the resilient tabs 83 to swing outward.

With reference to FIGS. 1, 3, 4, and 5, the driving tube 90 is mounted in the driving casing 80 and has a tube hole 91, an end board 92, and two side holes 94. The tube hole 91 is formed in a rear end of the driving tube 90. The end board 92 is formed on a front end of the driving tube 90 and has a through bore 93 defined through the end board 92 and communicating with the tube hole 91. The side holes 94 are defined radially in an outer surface of the driving tube 90 and communicate with the tube hole 91.

With reference to FIGS. 1, 3, 4, and 5, the engaging members A0 are mounted axially moveably in the driving casing 80 and are diametrically opposite each other and are disposed around a front end of the driving tube 90. Each engaging member A0 has engaging hooks A01 and two resilient locking portions A02. The engaging hooks A01 are formed on a front end of the engaging member A0, selectively extend respectively through the first through holes 26 in the inner casing 20 and are selectively engaged with the hooks 32 on the connection rod 30. The resilient locking portions A02 are formed on a rear end of the engaging member A0 and are engaged respectively with the engaging recesses 81 in the driving casing 80, and each locking portion A02 has a locking block A03.

With reference to FIGS. 1, 3, 4, and 5, the pushing rod A1 is mounted in the driving tube 90 and comprises a first rod segment A11, a second rod segment A12, and a middle board A13. The first rod segment A11 and the second rod segment A12 are aligned axially with each other. The first rod segment A11 is mounted through the through bore 93 in the end board 92. The middle board A13 is formed between the first rod segment A11 and the second rod segment A12 and has an outer diameter smaller than an inner diameter of the tube hole 91 of the driving tube 90 but larger than an inner diameter of the through bore 93 of the end board 92 and diameters of the first rod segment A11 and the second rod segment A12. The middle board A13 on the pushing rod A1 abuts against the two resilient engaging tabs 83 that extend through the side holes 94 in the driving tube 90 to hold the middle board A13 in position by the driving tube 90.

With reference to FIGS. 1, 3, 4, and 5, the rear spring A2 is mounted in the driving tube 90 and is mounted around the second rod segment A12 of the pushing rod A1. The rear spring A2 has two ends abutting the middle board A13 and the rear casing 70, respectively.

When the injection pen is in use, with reference to FIG. 1, the actuating mechanism 1 and the driving mechanism 2 are respectively assembled in advance, and a syringe 3 is mounted inside the actuating mechanism 1 and the driving mechanism 2 then is combined with the rear end of the actuating mechanism 1 to dispose the syringe 3 between the actuating mechanism 1 and the driving mechanism 2. With reference to FIGS. 4, 5, 6, and 7, the barrel 3B of the syringe 3 extends into the connection rod 30 of the actuating mechanism 1, and the needle 3A enclosed by a needle cap 3D extends into the needle hub 40. The needle cap 3D is engaged with the hook 521 on the connection tube 52 of the front cap 50. The pushing rod A1 of the driving mechanism 2 extends into the barrel 3B of the syringe 3 and abuts the piston 3C.

Figure 6:
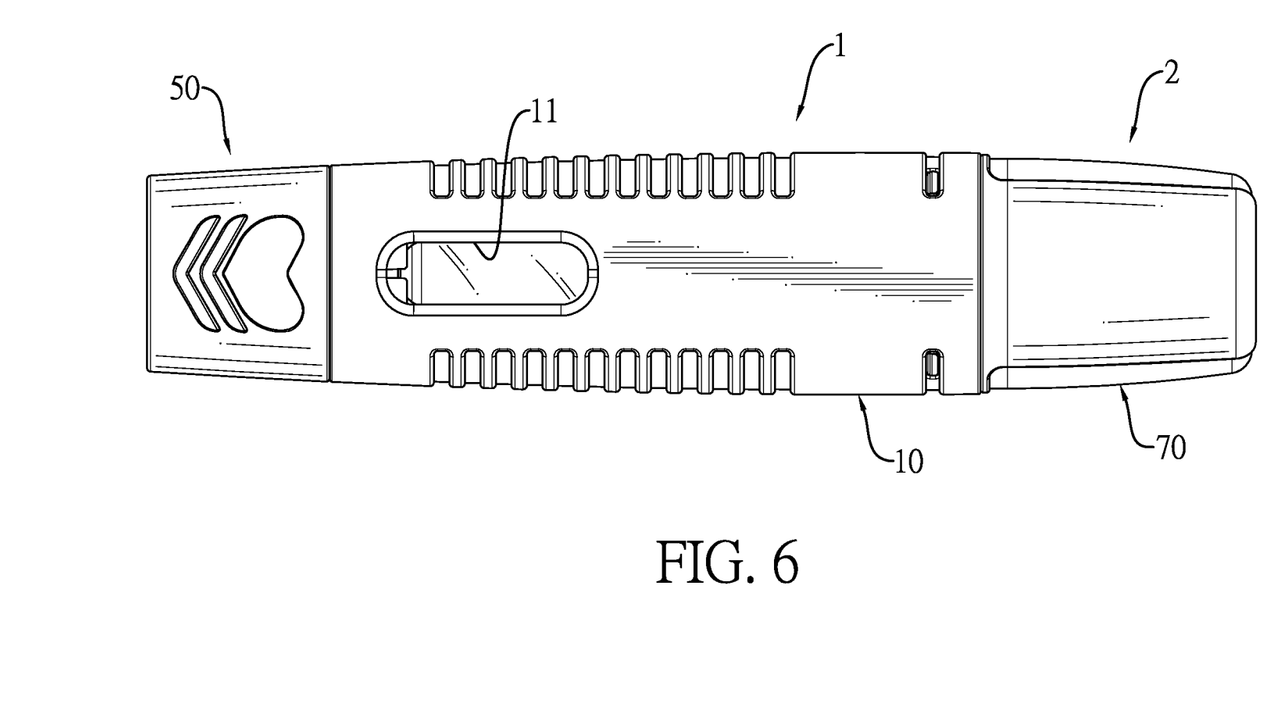
FIG. 6 is a top view of the injection pen in FIG. 1 combined with the syringe.
Figure 7:
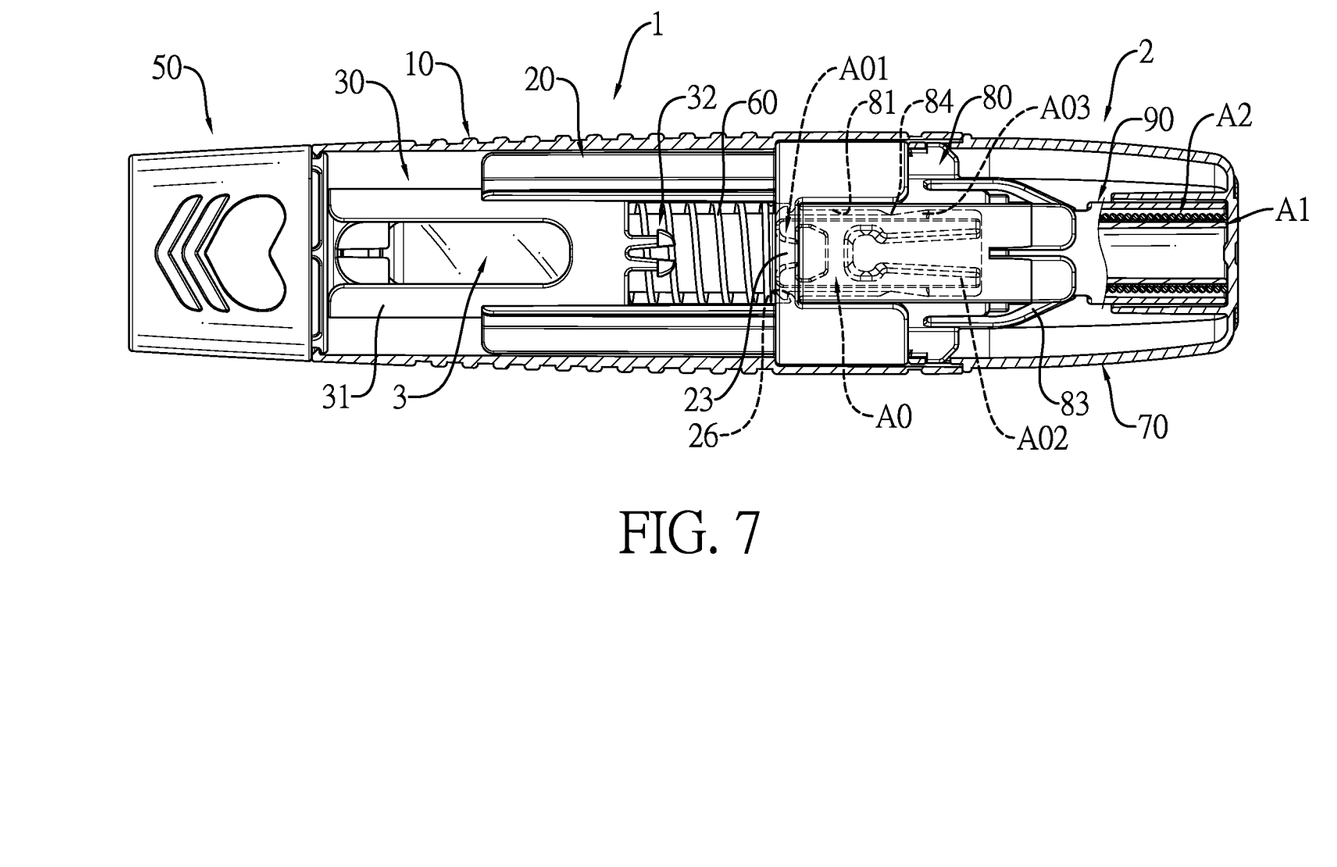
FIG. 7 is a top view in partial section of the injection pen in FIGS. 1 to 3 and 6 combined with the syringe.
Figure 8:
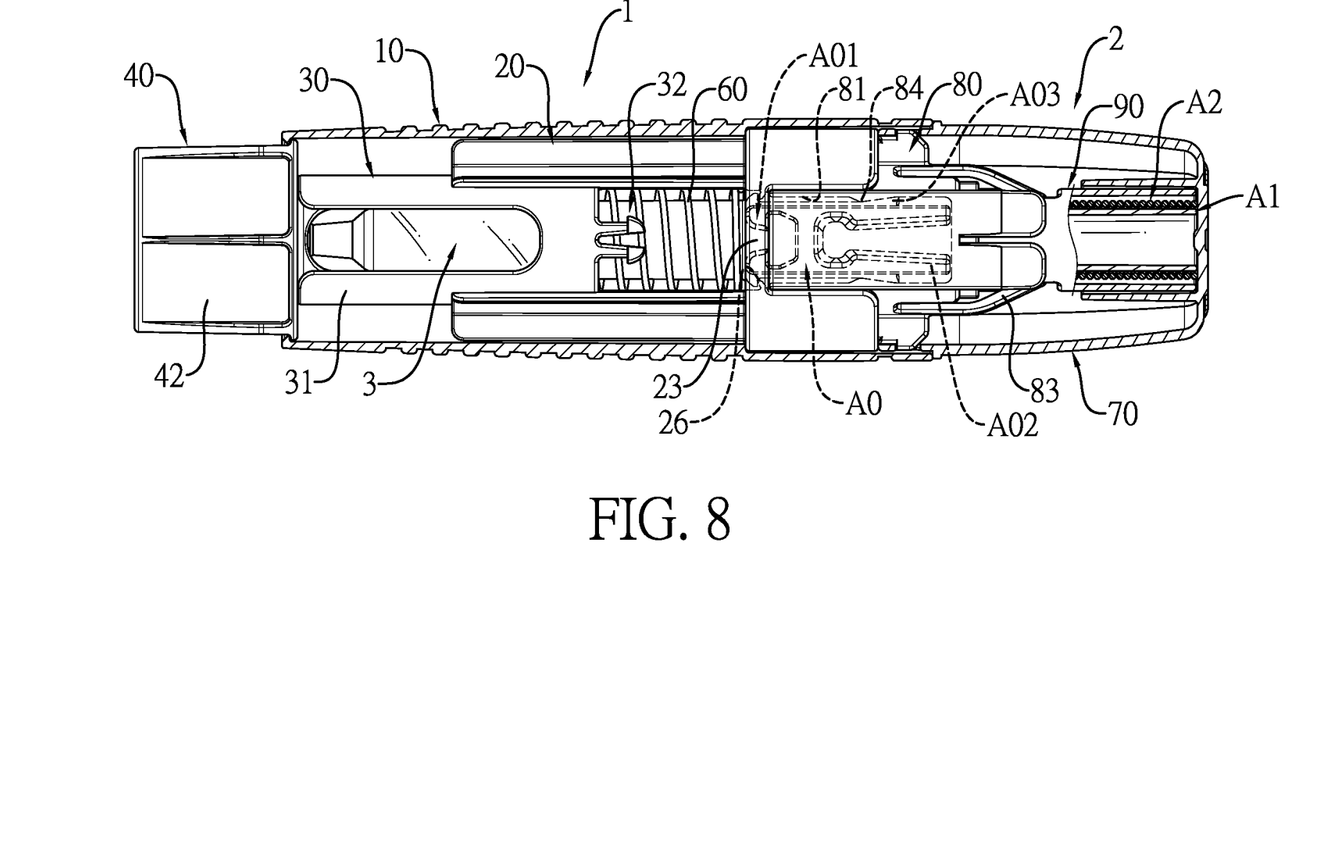
FIG. 8 is a top view in partial section of the injection pen in FIGS. 1 to 3 with the front cap being removed.

With reference to FIGS. 6 and 7, to inject medication by the injection pen, the front cap 50 is detached from the front end of the front casing 10, and the needle 3D of the syringe 3 will be removed simultaneously with the engagement with the hook 521 on the connection tube 52 of the front cap 50. At this time, with reference to FIGS. 8, 4, and 5, the needle hub 40 is disposed around the needle 3A of the syringe 3 to keep the needle 3A from being exposed.

Figure 9:
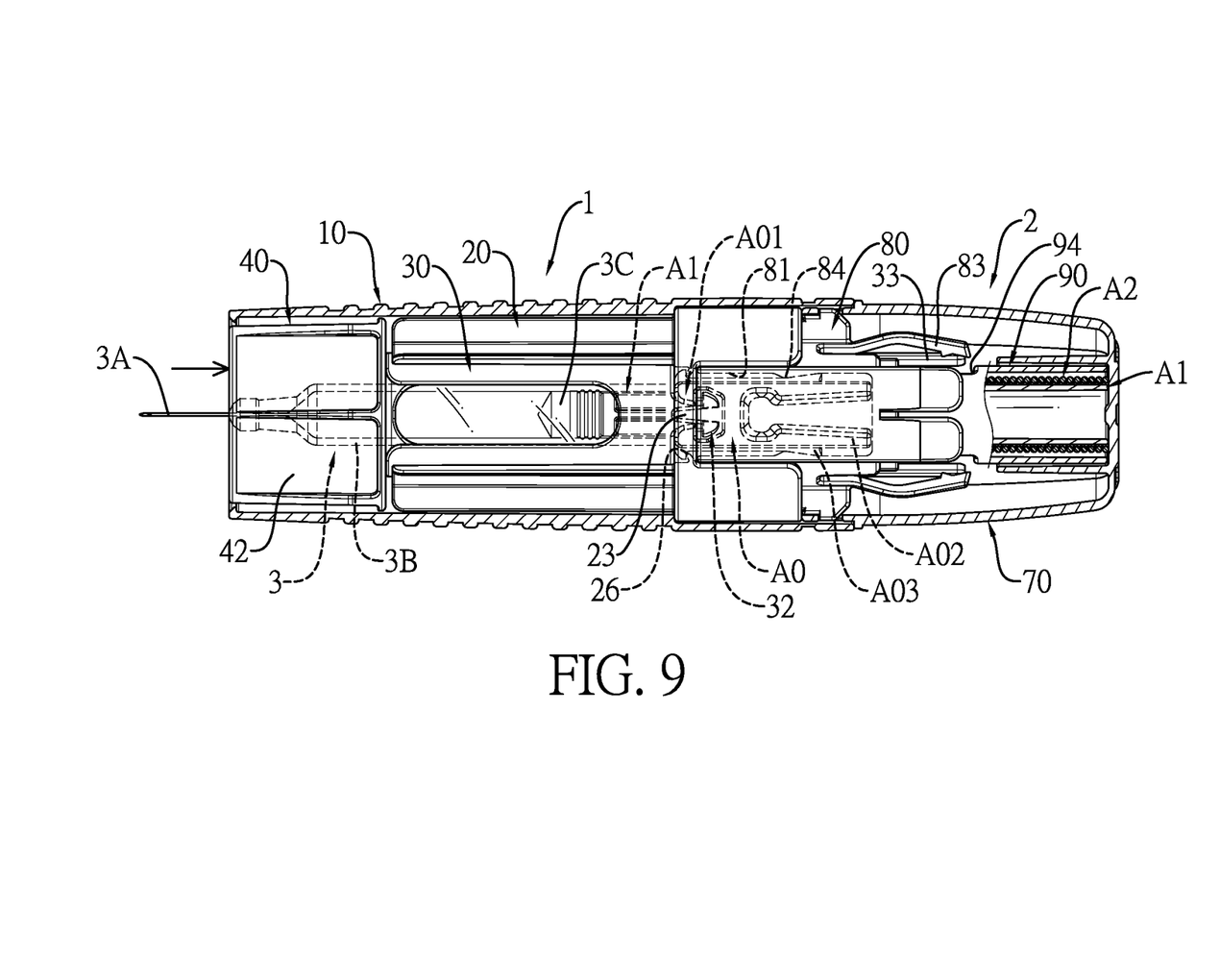
FIG. 9 is a top view in partial section of the injection pen in FIGS. 1 to 3 with the needle hub being pressed.
Figure 10:
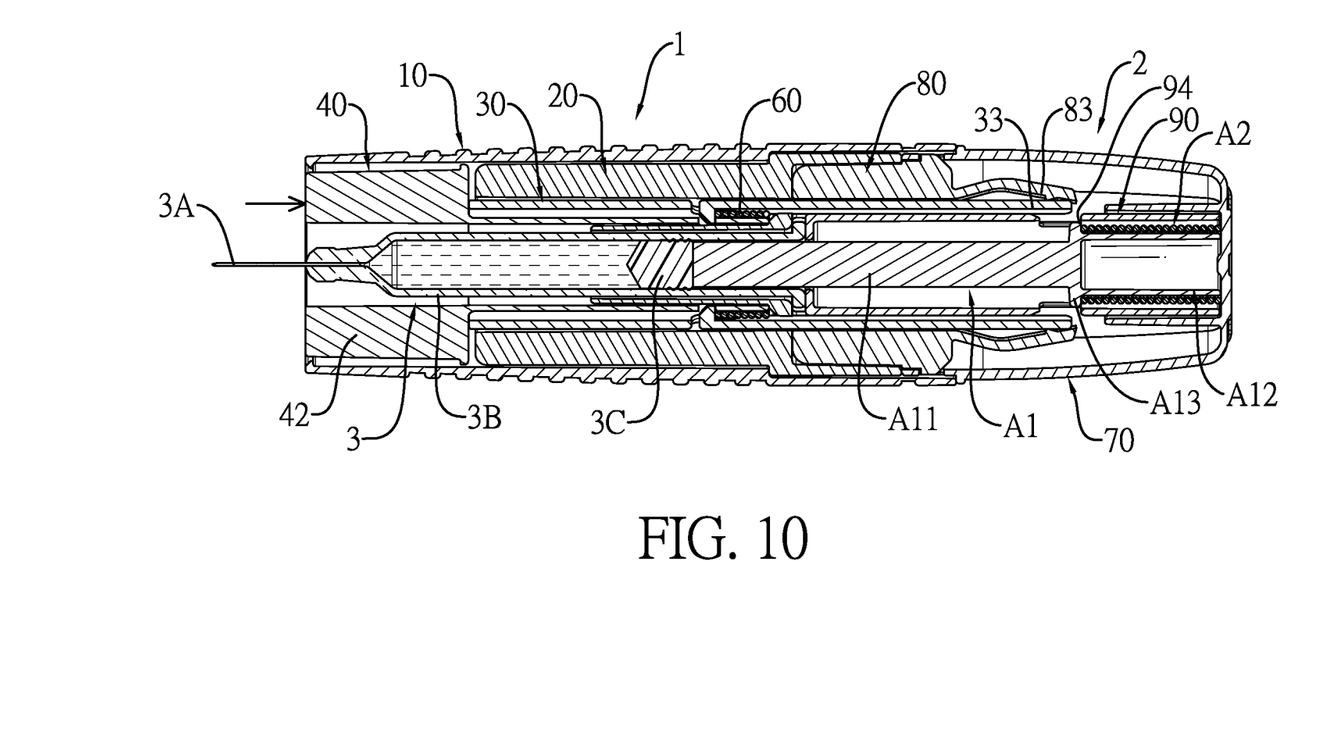
FIG. 10 is a cross sectional top view of the injection pen in FIGS. 1 to 3 with the needle hub being pressed.

With reference to FIGS. 9, 10, and 5, during injection, the needle hub 40 is pressed, and the front spring 60 is compressed via the connection rod 30 connected with the rear end of the needle hub 40. The needle hub 40 is retracted into the front casing 10, and the needle 3A of the syringe 3 is exposed. Accordingly, the needle 3A is ejected into the skin of a human body. With the needle hub 40 being pressed, the connection rod 30 is moved rearward by the needle hub 40 until the hooks 32 extend into the first through holes 26, and the hooks 32 are engaged with the engaging hooks A01 on the engaging members A0 to generate sounds to serve as a starting reminder. At this time, the actuating portions 33 on the connection rod 30 push against the engaging tabs 83 on the driving casing 80 to disengage the engaging tabs 83 from the side holes 94 in the driving tube 90 and the middle board A13 on the pushing rod A1 mounted in the driving tube 90. The compressed rear spring A2 is released, and the pushing rod A1 is pushed forward by the rear spring A2. Consequently, the pushing rod A1 pushes the piston 3C in the syringe 3 to move forward, and medication in the syringe is injected into the human body via the needle 3A. During the injection, the movement of the piston 3C is visible via the window 11 in the front casing 10.

Figure 11:
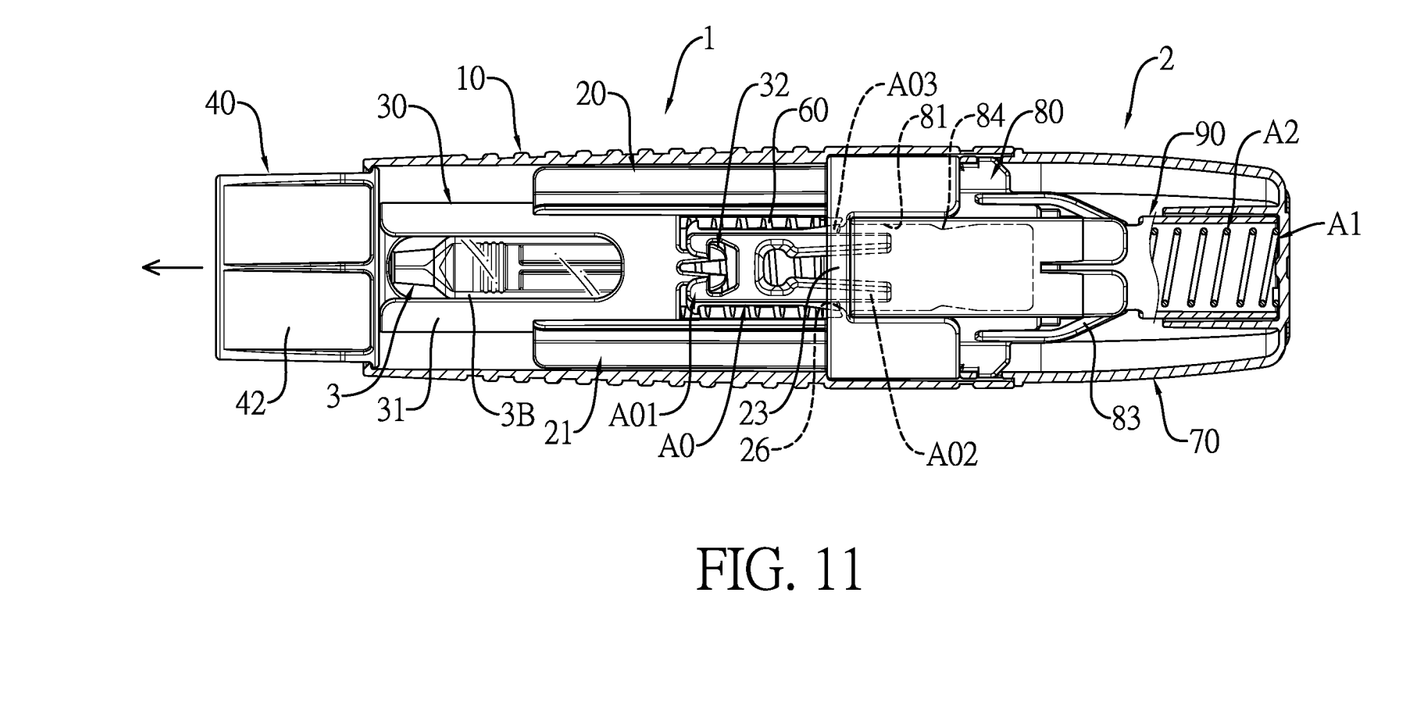
FIG. 11 is a top view in partial section of the injection pen in FIGS. 1 to 3 with the needle hub being released after the injection is completed.
Figure 12:
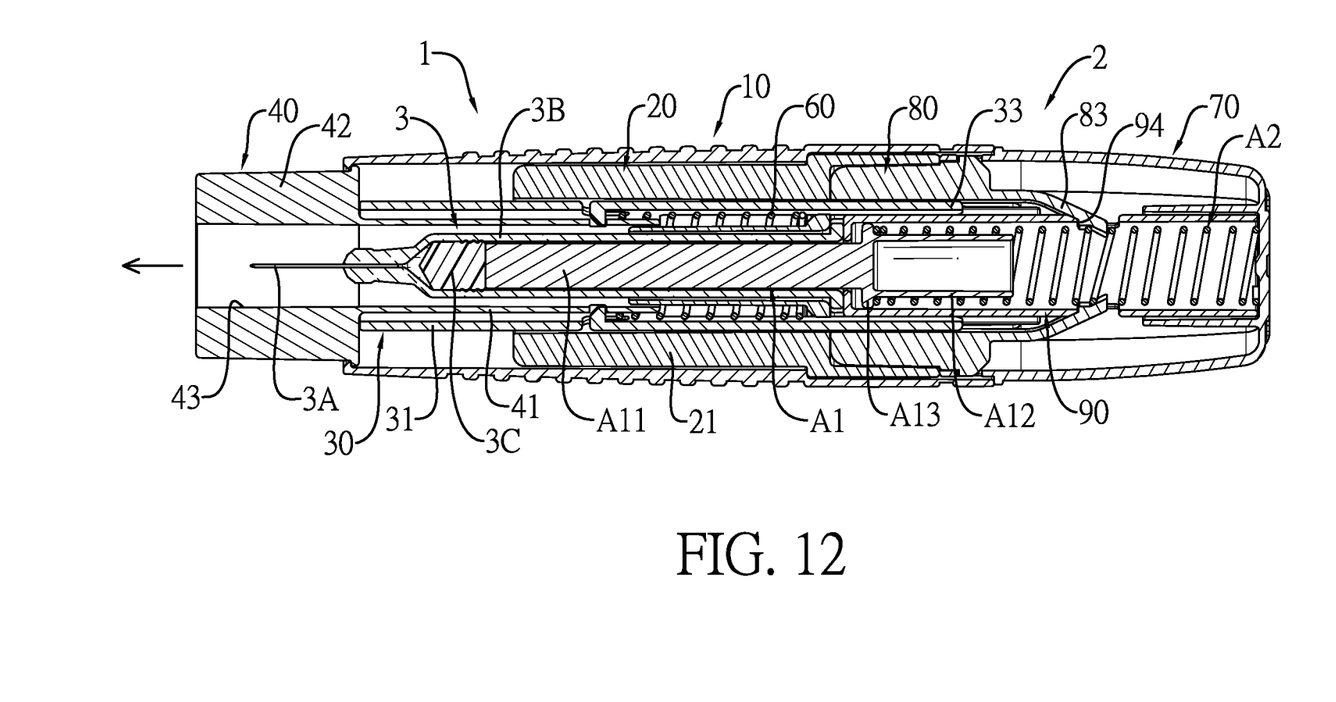
FIG. 12 is a cross sectional top view of the injection pen in FIGS. 1 to 3 with the needle hub being released after the injection is completed.

After the injection, the needle 3A is detached from the human body; with reference to FIGS. 11 and 12, the needle hub 40 and the connection rod 30 connected with the needle hub 40 are moved to the original positions by the front spring 60. At this time, the engaging members A0 are moved forward with the connection rods due to the connection with the connection rod 30 until the locking blocks A03 on locking portions A02 on the engaging members A0 abut the baffle 23 to generate sounds to serve as reminder of the termination of medication discharge. Accordingly, the engaging members A0 are secured on the baffle 23 and is kept from being moved rearward. With the fixed engaging members A0 and the connection rod 30, the needle hub 40 can be kept from being pressed and from being retracted into the front casing 10. Thus, the tip of the needle 3A can be enclosed inside the needle hub 40, so a user can be prevented from an accidental needle stick.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An injection pen comprising an actuating mechanism and a driving mechanism connected with the actuating mechanism, wherein the actuating mechanism comprises
- a front casing having an assembling space defined axially through the front casing;
- an inner casing mounted in the assembling space in the front casing and having a front segment, a rear segment, and a baffle disposed between the front segment and the rear segment and having an inner hole, two first through holes, and two second through holes, wherein the two first through holes and the two second through holes are located around the inner hole;
- a connection rod mounted moveably in the inner casing and comprising
   - a rod body having an axial hole defined axially through the rod body;
   - two hooks formed on a rear end of the rod body at positions corresponding respectively to the first through holes of the inner casing; and
   - two actuating portions formed on the rear end of the rod body and extending respectively through the second through holes of the inner casing;
- a needle hub mounted moveably in the front casing, connected with the connection rod, and having a tubular body and an outer sleeve formed around a front end of the tubular body, being located in front of a front end of the front casing, and being retractable into the front casing;
- a front cap mounted detachably around the outer sleeve of the needle hub and abutting the front end of the front casing; and
- a front spring mounted in the front segment of the inner casing, held between the actuating portions of the connection rod, and having two ends abutting the connection rod and the inner casing, respectively; and the driving mechanism comprises
- a rear casing being hollow, mounted on a rear end of the front casing;
- a driving casing mounted securely in the rear casing, extending into the front casing, and having a receiving space formed axially through the driving casing and two resilient engaging tabs;
- a driving tube mounted in the driving casing and having
   - a tube hole formed in a rear end of the driving tube;
   - an end board formed on a front end of the driving tube and having a through bore defined through the end board and communicating with the tube hole; and
   - two side holes defined radially in an outer surface of the driving tube, communicating with the tube hole, and selectively engaged with the resilient engaging tabs of the driving casing, wherein the actuating portions of the connection rod selectively extend into the driving tube to disengage the resilient engaging tabs from the side holes;
- two engaging members mounted in the driving casing and mounted around the front end of the driving tube, and each engaging member having
   - two engaging hooks formed on a front end of the engaging member, selectively extending respectively through the first through holes in the inner casing and selectively engaged with the hooks on the connection rod; and
   - two resilient locking portions formed on a rear end of the engaging member and engaged with the driving casing, wherein the engaging members are selectively pushed by the connection rod to move and to engage with the first through holes in the inner casing;
- a pushing rod mounted in the driving tube and having a first rod segment mounted through the through bore in the end board of the driving tube, a second rod segment, and a middle board formed between the first rod segment and the second rod segment and abutting the two resilient engaging tabs that are engaged with the side holes in the driving tube; and
- a rear spring mounted in the driving tube, mounted around the second rod segment of the pushing rod, and having two ends abutting the middle board and the rear casing, respectively.

2. The injection pen as claimed in claim 1, wherein the driving casing further has
- two engaging recesses defined in an inner surface of the driving casing and being diametrically opposite each other; and
- two guiding recesses defined in the inner surface of the driving casing and being diametrically opposite each other;

the engaging recesses and the guiding recesses in the driving casing are arranged in an alternate manner;
the resilient engaging tabs of the driving casing correspond respectively to the guiding recesses in position;
the actuating portions of the connection rod are mounted respectively through the guiding recesses and selectively push the actuating portions, respectively, to swing outward; and
the resilient locking portions of each engaging member are engaged detachably with the engaging recesses in the driving casing.

3. The injection pen as claimed in claim 2, wherein
the two first through holes and the two second through holes in the inner casing are arranged in an alternate manner;
the first through holes are diametrically opposite each other;
the second through holes are diametrically opposite each other;
the baffle of the inner casing has an inner tube formed on a front side of the baffle and extending into the front segment of the inner casing;

the inner hole in the baffle extends into the inner tube; and
the front spring is mounted around the inner tube.

4. The injection pen as claimed in claim 3, wherein
the front casing has a window formed radially in an outer surface of a front segment of the front casing and communicating with the assembling space;
the front segment of the inner casing comprises two wings diametrically opposite each other and spaced at a spaced interval;
the interval between the wings is equal to a width of the window in the front casing; and
the connection rod has an elongated hole defined in the rod body of the connection rod and corresponding to the window in the front casing in position.

5. The injection pen as claimed in claim 4, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab;
the driving casing has two fixing blocks formed on an outer surface of the driving casing and engaged respectively with the fixing hole in the rear casing to securely mount the driving casing in the rear casing;
the rod body of the connection rod further has two resilient tabs formed on an outer surface of the rod body and diametrically opposite each other; and
the tubular body of the needle hub further has two tab holes defined in the tubular body and engaged respectively with the resilient tabs on the rod body of the connection rod to connect the connection rod with the needle hub.

6. The injection pen as claimed in claim 3, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab; and
the driving casing has two fixing blocks formed on an outer surface of the driving casing and engaged respectively with the fixing hole in the rear casing to securely mount the driving casing in the rear casing.

7. The injection pen as claimed in claim 3, wherein
the front cap comprises
a cap body mounted around the outer sleeve of the needle hub and having a closed front end and an open rear end abutting the front end of the front casing; and
a connection tube formed in the cap body, extending out of the open rear end of the cap body, extending into the tubular body of the needle hub, and having a rear end provided with a hook and at least one slit defined in the rear end of the connection tube.

8. The injection pen as claimed in claim 2, wherein
the front casing has a window formed radially in an outer surface of a front segment of the front casing and communicating with the assembling space;
the front segment of the inner casing comprises two wings diametrically opposite each other and spaced at a spaced interval;
the interval between the wings is equal to a width of the window in the front casing; and
the connection rod has an elongated hole defined in the rod body of the connection rod and corresponding to the window in the front casing in position.

9. The injection pen as claimed in claim 8, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab;
the driving casing has two fixing blocks formed on an outer surface of the driving casing and engaged respectively with the fixing hole in the rear casing to securely mount the driving casing in the rear casing;
the rod body of the connection rod further has two resilient tabs formed on an outer surface of the rod body and diametrically opposite each other; and
the tubular body of the needle hub further has two tab holes defined in the tubular body and engaged respectively with the resilient tabs on the rod body of the connection rod to connect the connection rod with the needle hub.

10. The injection pen as claimed in claim 2, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab; and
the driving casing has two fixing blocks formed on an outer surface of the driving casing and engaged respectively with the fixing hole in the rear casing to securely mount the driving casing in the rear casing.

11. The injection pen as claimed in claim 2, wherein
the front cap comprises
a cap body mounted around the outer sleeve of the needle hub and having a closed front end and an open rear end abutting the front end of the front casing; and
a connection tube formed in the cap body, extending out of the open rear end of the cap body, extending into the tubular body of the needle hub, and having a rear end provided with a hook and at least one slit defined in the rear end of the connection tube.

12. The injection pen as claimed in claim 1, wherein
the two first through holes and the two second through holes in the inner casing are arranged in an alternate manner;
the first through holes are diametrically opposite each other;
the second through holes are diametrically opposite each other;
the baffle of the inner casing has an inner tube formed on a front side of the baffle and extending into the front segment of the inner casing;
the inner hole in the baffle extends into the inner tube; and
the front spring is mounted around the inner tube.

13. The injection pen as claimed in claim 12,
wherein the front casing has a window formed radially in an outer surface of a front segment of the front casing and communicating with the assembling space;
the front segment of the inner casing comprises two wings diametrically opposite each other and spaced at a spaced interval;
the interval between the wings is equal to a width of the window in the front casing; and
the connection rod has an elongated hole defined in the rod body of the connection rod and corresponding to the window in the front casing in position.

14. The injection pen as claimed in claim 13, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab;
the driving casing has two fixing blocks formed on an outer surface of the driving casing and engaged respectively with the fixing hole in the rear casing to securely mount the driving casing in the rear casing;
the rod body of the connection rod further has two resilient tabs formed on an outer surface of the rod body and diametrically opposite each other; and
the tubular body of the needle hub further has two tab holes defined in the tubular body and engaged respectively with the resilient tabs on the rod body of the connection rod to connect the connection rod with the needle hub.

15. The injection pen as claimed in claim 12, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab; and
the driving casing has two fixing blocks formed on an outer surface of the driving casing and engaged respectively with the fixing hole in the rear casing to securely mount the driving casing in the rear casing.

16. The injection pen as claimed in claim 12, wherein the front cap comprises
a cap body mounted around the outer sleeve of the needle hub and having a closed front end and an open rear end abutting the front end of the front casing; and
a connection tube formed in the cap body, extending out of the open rear end of the cap body, extending into the tubular body of the needle hub, and having a rear end provided with a hook and at least one slit defined in the rear end of the connection tube.

17. The injection pen as claimed in claim 1, wherein
the front casing has a window formed radially in an outer surface of a front segment of the front casing and communicating with the assembling space;
the front segment of the inner casing comprises two wings diametrically opposite each other and spaced at a spaced interval;
the interval between the wings is equal to a width of the window in the front casing; and
the connection rod has an elongated hole defined in the rod body of the connection rod and corresponding to the window in the front casing in position.

18. The injection pen as claimed in claim 17, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab;
the driving casing has two fixing blocks formed on an outer surface of the driving casing and engaged respectively with the fixing hole in the rear casing to securely mount the driving casing in the rear casing;
the rod body of the connection rod further has two resilient tabs formed on an outer surface of the rod body and diametrically opposite each other; and
the tubular body of the needle hub further has two tab holes defined in the tubular body and engaged respectively with the resilient tabs on the rod body of the connection rod to connect the connection rod with the needle hub.

19. The injection pen as claimed in claim 1, wherein
the front casing further has two engaging holes defined in a rear segment of the front casing;
the rear casing has two extension tabs formed on a front end of the rear casing and extending into the rear segment of the front casing;
each extension tab has an engaging protrusion selectively engaged with a respective one of the engaging holes in the front casing and a fixing hole defined in the extension tab; and
the driving casing has two fixing blocks formed on an outer surface of the driving casing and engaged respectively with the fixing hole in the rear casing to securely mount the driving casing in the rear casing.

20. The injection pen as claimed in claim 1, wherein the front cap comprises
a cap body mounted around the outer sleeve of the needle hub and having a closed front end and an open rear end abutting the front end of the front casing; and
a connection tube formed in the cap body, extending out of the open rear end of the cap body, extending into the tubular body of the needle hub, and having a rear end provided with a hook and at least one slit defined in the rear end of the connection tube.

* * * * *